United States Patent [19]

Ams

[11] Patent Number: 5,031,454
[45] Date of Patent: Jul. 16, 1991

[54] IMAGE GENERATOR WITH HUMIDITY DETECTION AND CORRECTION MEANS

[75] Inventor: Felix Ams, Kämpfelbach, Fed. Rep. of Germany

[73] Assignee: Richard Wolf GmbH, Knittlingen, Fed. Rep. of Germany

[21] Appl. No.: 484,596

[22] Filed: Feb. 23, 1990

[30] Foreign Application Priority Data

Mar. 20, 1989 [DE] Fed. Rep. of Germany ....... 3909090

[51] Int. Cl.$^5$ .................................................. G01N 37/00
[52] U.S. Cl. .................................................. 73/336.5
[58] Field of Search .................... 73/336.5, 336, 335, 73/29.02; 340/602

[56] References Cited

U.S. PATENT DOCUMENTS

| | | | |
|---|---|---|---|
| 3,522,732 | 8/1970 | Bauer | 73/336.5 |
| 3,557,619 | 1/1971 | Hershler | 73/336.5 |
| 3,886,797 | 6/1975 | Bauer | 73/335 |
| 4,894,532 | 1/1990 | Peterson et al. | 73/336.5 X |

FOREIGN PATENT DOCUMENTS 1564479  4/1969  France ............................... 73/336.5

Primary Examiner—Hezron E. Williams
Assistant Examiner—Joseph W. Roskos
Attorney, Agent, or Firm—Panitch Schwarze Jacobs & Nadel

[57] ABSTRACT

In the sealed interior of an image-generating recording or transmitting device, for example an endoscope, videoscope, endo-technoscope or the alike, there is provided at least one sensor which responds to minute changes in atmospheric humidity. The actual value of the humidity is compared by an electronic monitoring device with a maximum admissible limit humidity value. If the actual humidity value reaches a preselectable limit value range, an analog signal is displayed and, if the maximum admissible limit value is exceeded, a signal is generated to actuate an air pump to load the interior of the recording and/or transmitting device with excess air pressure.

15 Claims, 3 Drawing Sheets

IMAGE GENERATOR WITH HUMIDITY DETECTION AND CORRECTION MEANS

FIELD OF THE INVENTION

This invention relates to improved image-generating recording and/or transmitting means such as endoscopes, videoscopes, techno-endoscopes, endo-cameras or the like which have sealed cavities. As a result of improper use of, or damage to, said recording means atmospheric humidity or liquid can penetrate into the sealed cavity and under certain circumstances can severely impair, or indeed prevent, the functioning of the image generating means so that expensive and labour-intensive repairs must be carried out.

BACKGROUND OF THE INVENTION

For the detection of damage caused to an image-generating instrument as a result of atmospheric humidity penetrating a sealed cavity thereof, DE-A-33 46 850 teaches that the instrument should be immersed in a liquid so that air bubbles emerge from the damaged cavity thereby precisely indicating the site of the damage so that it can be repaired.

Such a method of locating damage is aleatory since such tests are not usually carried out at regular intervals.

SUMMARY OF THE INVENTION

An object of the invention is to provide an improved image-generating recording and/or transmitting means wherein even the penetration of minute quantities of atmospheric humidity into the sealed cavity can at all times be detected by the user and the resultant damage teen eliminated.

According to the present invention image-generating recording and/or transmitting means such as an endoscope, a techno-endoscope, a videoscope or an endo-camera, has provided in the sealed cavity thereof at least one sensor which responds to the penetration of atmospheric humidity into the cavity and is connected to downstream electronics means in such a way that any change in the signal emitted by the sensor, or the actual humidity value is detected and evaluated and, upon approximation of the actual value to a preselectable limit value, the signal value or its difference relative to a maximum admissible limit value, is produced as an analog display and, if the admissible limit value is exceeded, an appropriate signal is generated and a pump connected to the interior of the recording or transmitting means is put into operation to maintain or reduce the air humidity content.

When atmospheric humidity penetrates the pump prevents further humidity or liquid from entering the cavity by loading said interior with excess air pressure.

DETAILED DESCRIPTION OF THE INVENTION

Figure 1:
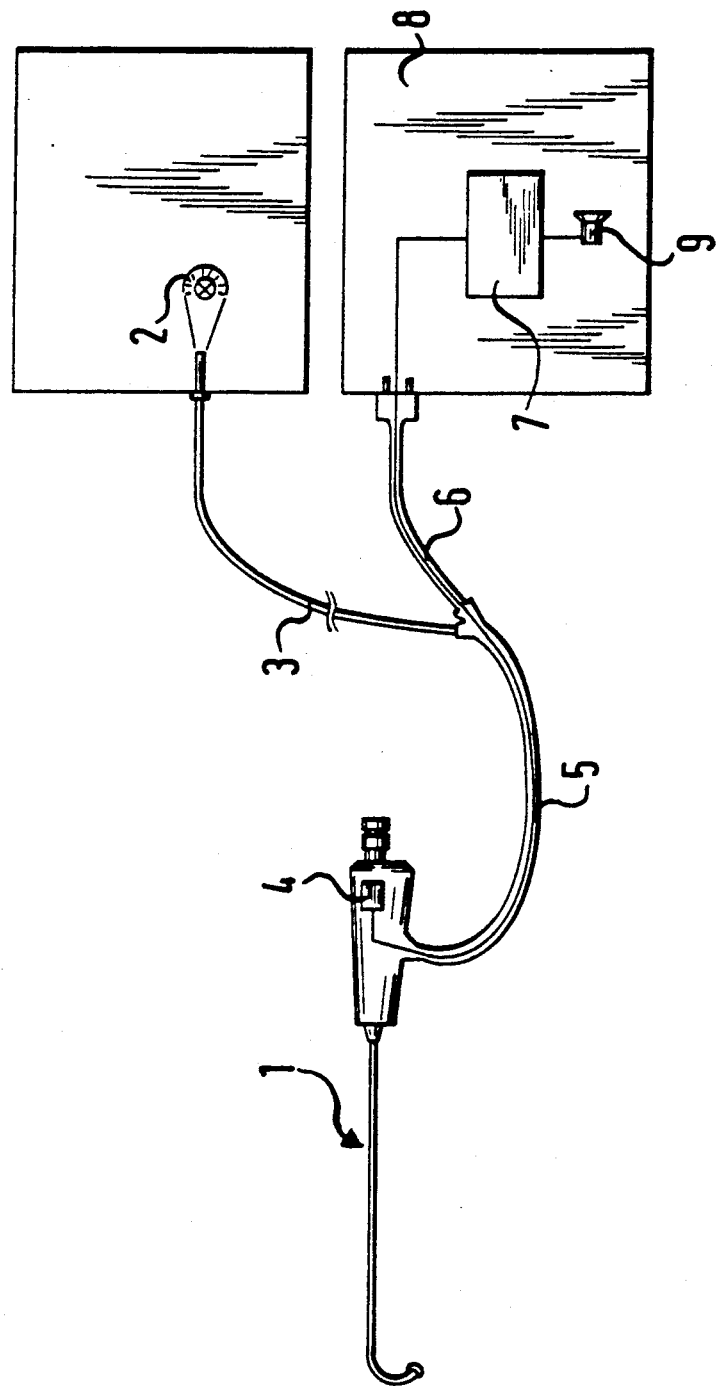
FIG. 1 is a diagrammatic side view of a flexible endoscope having a light source and an electronic device for monitoring air humidity in a cavity of the endoscope.
Figure 3:
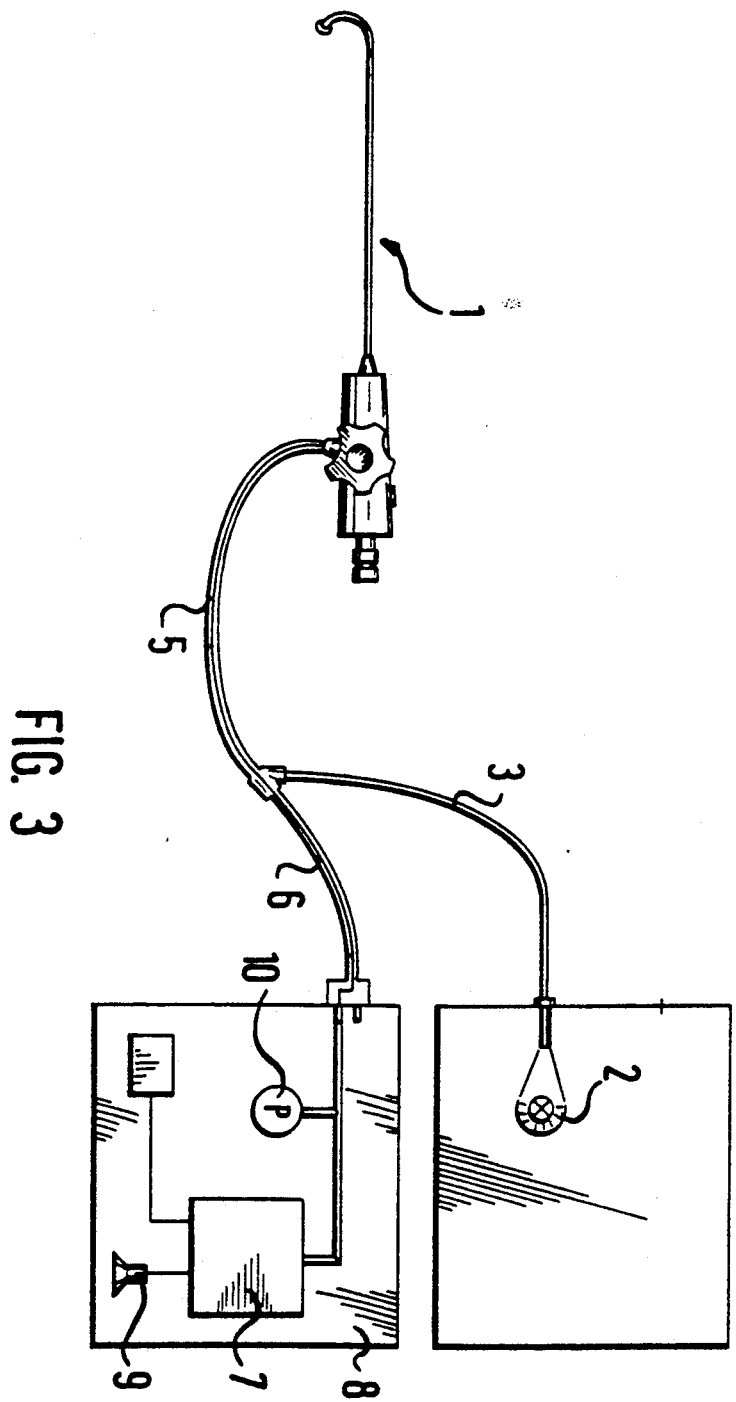
FIG. 3 is a similar view to that of FIG. 1 but showing a pump integrated in the electronic pumptoring device, for generating excess air pressure.

Reference will now be made to FIGS. 1 and 3. An image-generating instrument in the form of an endoscope 1 has attached thereto a light source 2 for transmitting light by way of a fibre-optic light guide 3 through the endoscope 1 to illuminate an object to be examined.

A sensor 4 disposed in a sealed cavity in the endoscope 1 is such as to be responsive even to very small quantities of humidity in said cavity and is connected by means of electrical leads 5 and 6 to an electronics evaluation comparator circuit 7 of an electronic monitoring device 8. The actual humidity value measured by the sensor 4 when the humidity of air in the sealed cavity increases, is compared be means of the circuit 7 with a predetermined maximum admissible humidity value. If the actual humidity valve, as measured by the sensor 4 measures a preselectable limit value range, the actual value or the difference between the actual value and maximum admissible limit value is displayed on an analogue display device 11 connected to the circuit 7. If, however, the actual humidity value as measured by the sensor 4 exceeds the maximum admissible limit value, an acoustic signalling device 9 connected to the comparator circuit 7 is activated thereby to emit an acoustic warning signal and an excess air pressure pump 10 (FIG. 3) connected to the interior of the endoscope 1 is started in order to prevent any further humidity from penetrating into the interior of the endoscope 1.

Figure 2:
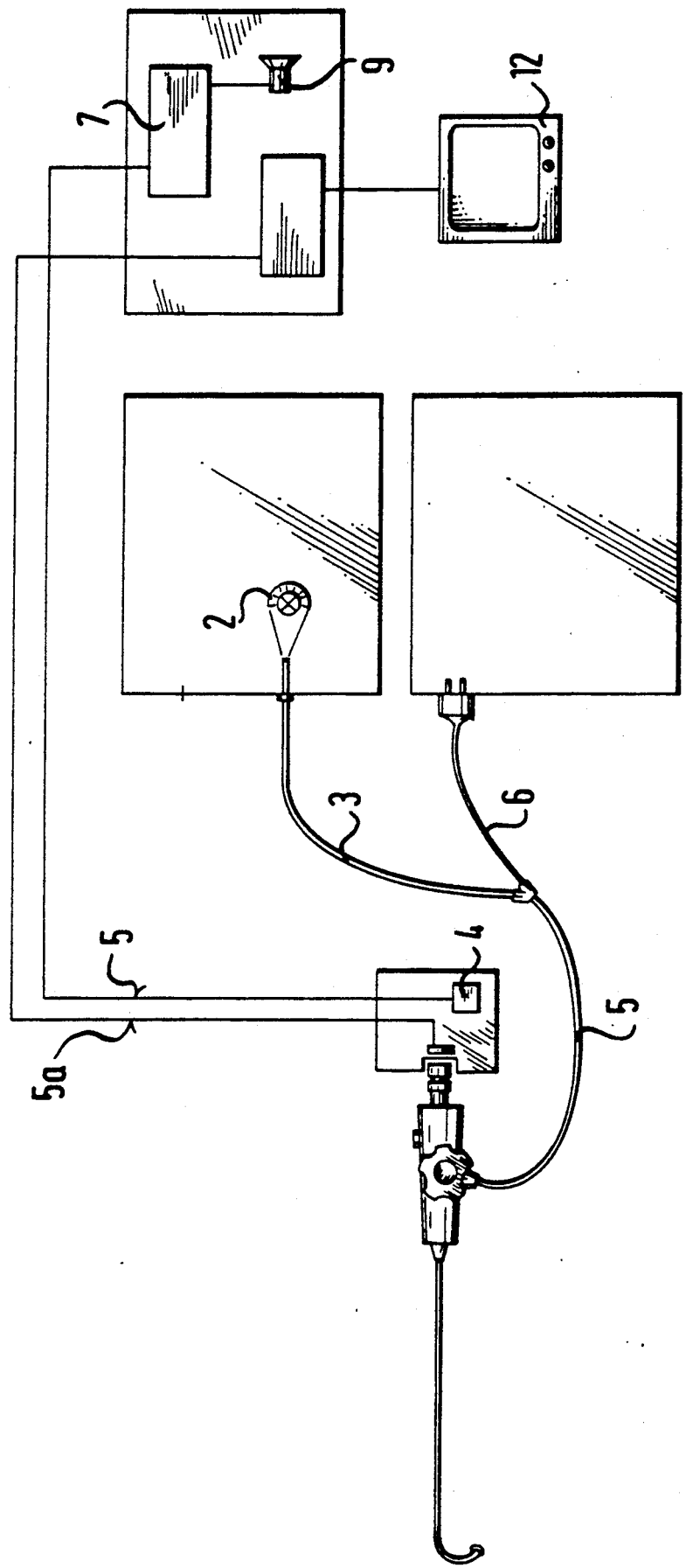
FIG. 2 is a similar view to that of FIG. 1 but showing an atmospheric camera connected to the endoscope.

As shown in FIG. 2, the sensor 4 is disposed in the interior of an endo-camera 13, instead of being disposed in the interior of the endoscope 1. The endo-camera 13 is connected to a monitor 14 or display screen 12 by way of a lead 5a. The sensor 4 cooperates with the comparator circuit 7 of the monitoring device 8, in the manner described above with reference to FIGS. 1 and 3.

The sensor 4 may be disposed in the direct vicinity of a solid state image recorder of the endo-camera 13.

Instead of a single sensor 4 a plurality of mutually spaced sensors may be disposed in the interior of the endoscope 1 or the endo-camera 13.

The sensor or sensors may be provided in a sealed cavity in a techno-endoscope or a videoscope, for example, instead of in the endoscope 1 or the endo-camera 13.

The sensor or sensors included in the evaluation circuit 7 as well as suitable acoustic or optical means for indicating changes in air atmospheric humidity and/or the exceeding of a preselectable air humidity limit value may be disposed in the interior of the endoscope or the endo-camera.

What is claimed is:

1. In an image-generating means having a sealed cavity therein, the improvement comprising:
    at least one sensor in said cavity responsive to the presence of humidity therein to emit a signal having a value indicative of the actual value of humidity in said cavity;
    a display device actuable to indicate the value of said humidity;
    an air pump connected to the interior of said apparatus and being actuable to control the atmospheric humidity of said cavity; and
    electronic means connected to said at least one sensor and to said pump and to said display device, for detecting and evaluating changes in said signal in relation to a maximum admissible humidity limit value, for actuating said display device where said actual value approximates to a preselectable humidity limit value and for actuating said pump where said actual value exceeds the maximum admissible humidity limit value.

2. The improvement as claimed in claim 1, wherein said at least one sensor is disposed directly in the vicinity of a solid state image recorder of said image-generating means.

3. The improvement claimed in claim 1, wherein a plurality of said sensors are disposed in said interior in mutually spaced relationship.

4. The improvement claimed in claim 1, wherein said at least one sensor included in said electronic means and suitable acoustic means for indicating changes in said humidity are disposed in said interior.

5. The improvement as claimed in claim 1, wherein said pump is actuable by said electronic means to load said interior with air under pressure.

6. The improvement as claimed in claim 1, wherein said display device is an analogue display device.

7. The improvement claimed in claim 1, wherein said display device is actuable by said electronic means to display the difference between the actual value of said signal and said maximum admissible limit value.

8. The improvement claimed in claim 1, wherein said display device is actuable by said electronic means to display the actual value of said signal.

9. The improvement claimed in claim 1, wherein said at least one sensor included in said electronic means and suitable optical means for indicating changes in said humidity are disposed in said interior.

10. The improvement claimed in claim 1, wherein said image-generating means is an endoscope.

11. The improvement claimed in claim 1, wherein said image-generating means is a techno-endoscope.

12. The improvement claimed in claim 1, wherein said image-generating means is a videoscope.

13. The improvement claimed in claim 1, wherein said image-generating means is an endo-camera.

14. In an image-generating recording means having sealed cavity therein, the improvement comprising:
- at least one sensor in said cavity responsive to the presence of humidity therein to emit a signal having a value indicative of the actual value of humidity in said cavity;
- a display device actuable to indicate the value of said humidity;
- an air pump connected to the interior of said apparatus and being actuable to control the atmospheric humidity of said cavity; and
- electronic means connected to said at least one sensor and to said pump and to said display device, for detecting and evaluating changes in said signal in relation to a maximum admissible humidity limit value, for actuating said display device where said actual value approximates to a preselectable humidity limit value and for actuating said pump where said actual value exceeds the maximum admissible humidity limit value.

15. In an image-generating transmitting means having a sealed cavity therein, the improvement comprising:
- at least one sensor in said cavity responsive to the presence of humidity therein to emit a signal having a value indicative of the actual value of humidity in said cavity;
- a display device actuable to indicate the value of said humidity;
- an air pump connected to the interior of said apparatus and being actuable to control the atmospheric humidity of said cavity; and
- electronic means connected to said at least one sensor and to said pump and to said display device, for detecting and evaluating changes in said signal in relation to a maximum admissible humidity limit value, for actuating said display device where said actual value approximates to a preselectable humidity limit value and for actuating said pump where said actual value exceeds the maximum admissible humidity limit value.

* * * * *